United States Patent [19]

Fenton

[11] Patent Number: 4,460,359
[45] Date of Patent: Jul. 17, 1984

[54] CLAMP CLOSURE ASSEMBLY

[75] Inventor: Leonard Fenton, Beachwood, Ohio

[73] Assignee: Marlen Manufacturing and Development Co., Bedford, Ohio

[21] Appl. No.: 368,363

[22] Filed: Apr. 14, 1982

[51] Int. Cl.³ .................. A61M 31/00; A61M 1/00
[52] U.S. Cl. .................... 604/277; 604/332; 24/30.5 P
[58] Field of Search .............. 604/332–345, 604/277; 24/30.5 R, 30.5 P, 30.5 L, 17 AP, 67.9, 129 B; 248/74.1, 74.3, 74.5; 150/6, 7, 3

[56] References Cited

U.S. PATENT DOCUMENTS

| | | | |
|---|---|---|---|
| 1,982,813 | 12/1934 | Jacobi | 150/7 |
| 2,528,192 | 10/1950 | Urban | 150/7 |
| 2,654,169 | 10/1953 | Dryden | 24/17 AP |
| 2,818,069 | 12/1957 | Fenton | 604/338 |
| 2,818,871 | 1/1958 | Beaudry | 248/74 PB |
| 3,169,004 | 2/1965 | Rapata | 248/74.5 |
| 3,315,324 | 4/1967 | Ward | 24/30.5 P |
| 4,233,977 | 11/1980 | Mattson | 604/344 |
| 4,414,717 | 11/1983 | Payne | 24/30.5 R |

Primary Examiner—C. Fred Rosenbaum
Assistant Examiner—J. L. Kruter
Attorney, Agent, or Firm—Pearne, Gordon, Sessions, McCoy, Granger & Tilberry

[57] ABSTRACT

A closure clamp for the drainage outlet of an ostomy bag is disclosed. The clamp comprises an elongated strip of stiffly flexible plastic material having a centrally located winding portion and a pair of closure wings integral with and extending from the ends of said winding portion. Each wing is hinged to the winding portion by thinned zones of separation so that the wings may be folded to overlie the winding portion. The centrally located winding portion has an integral arm parallel thereto and spaced therefrom to serve as an initial gripping member to facilitate the winding operation and the wings are provided with interengaging attachment members to hold the wings together in a clamped position to securely maintain the bag in its wound configuration about the winding portion.

5 Claims, 10 Drawing Figures

CLAMP CLOSURE ASSEMBLY

BACKGROUND OF THE INVENTION

This invention relates to a reusable, resealable ileostomy or colostomy bag or pouch which may be emptied without removing the bag from the stoma of the user and, more particularly, to a closure clamp for such a bag to permit the drain opening of the bag to be easily closed and resealed while the bag is mounted on the stoma of the user.

In order to successfully perform the function of collecting fecal matter from a patient, the pouches must be constructed so that they cause a minimum of discomfort to the user, prevent odor, and provide a sanitary receptacle which may be easily emptied and resealed.

Typical fecal pouches which may employ a clamp closure according to the present invention are formed with a double-walled structure having a completely sealed air space between the inner and outer walls of the pouch. The pouch has an inlet opening formed in and through an upper portion which is adapted to be attached to a conventional pouch supporting belt worn by the user. The pouch is generally flat, to be worn unobtrusively by the user, and is necked down at its lower end to form a drainage opening which is adapted to be closed by a clamp or by an integral sealing arrangement. Such a pouch is illustrated in U.S. Pat. No. 3,385,298.

A variety of clamps or integral sealing devices have been proposed to effectively seal the drainage end of ostomy pouches. One such arrangement is shown and described in U.S. Pat. No. 3,825,005. That patent discloses the provision of ribs and channels within the drainage opening of the bag which interlock by finger pressure to provide an acceptable seal while permitting quick opening thereof. The use of the arrangement disclosed in that patent is advantageous, since it is not bulky, and therefore is nonirritating to the user of such a bag. Moreover, since the closure is integral with the bag, the closure assembly necessarily adds to the cost of the item. Additionally, the channel end rib arrangement must be carefully cleaned to prevent the buildup of fecal matter at the bag opening.

A further bag closure arrangement is shown in U.S. Pat. No. 3,690,320 wherein a Velco fastener is employed as a sealing member. While this arrangement provides many of the advantages of U.S. Pat. No. 3,825,005, it also possesses some of the disadvantages.

Probably the most popular arrangement in use today is a plastic bar which is dimensioned to extend across the width of the bag drain opening. The bar is provided with locking teeth at its ends which are adapted to engage the ends of a separate clamping bar so that the bag end may be wound about the first-mentioned bar and the locking bar may then be engaged by the locking teeth. While this arrangement provides an effective and compact seal, it includes two separate members one of which may be frequently lost. In fact, a manufacturer of such a clamping member provides rubber bands in the package containing the clamping member so that the user may wind the bands about the winding bar if the clamping bar is lost. Ostomy bag users, moreover, improvise clamping members by employing paper gripping clamps or hair barrettes as clamping devices. Obviously, such clamps are bulky and unsanitary.

SUMMARY OF THE INVENTION

This invention provides a bag clamp closure assembly which includes a one-piece clamp adapted to securely fasten the drainage end of an ostomy bag with a compact, effective seal which is sanitary and which is easy to use. According to this invention, the clamp comprises an elongated strip of stiffly flexible plastic material having a centrally located winding portion and a pair of closure wings integral with and extending from the ends of the winding portion. Each wing is hinged to the winding portion by thinned zones of separation so that the wings may be folded to overlie the winding portion. The centrally located winding portion has an integral arm parallel thereto and spaced therefrom to serve as an initial gripping member to facilitate the winding operation and the wings are provided with interengaging attachment members to hold the wings together in a clamped position to securely maintain the bag in its wound configuration about the winding portion. The winding portion and the wings may be provided with indicia to facilitate the order of steps involved in winding and clamping the drainage end of the bag.

DETAILED DESCRIPTION OF THE INVENTION

Figure 1:
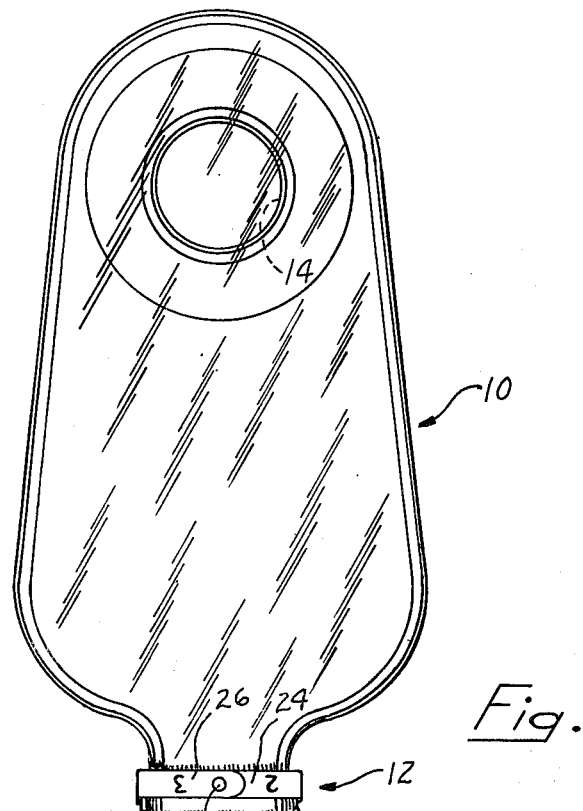
FIG. 1 is an elevational view of an ostomy bag showing the clamp closure assembly according to this invention in its clamping and sealing condition.
Figure 2:
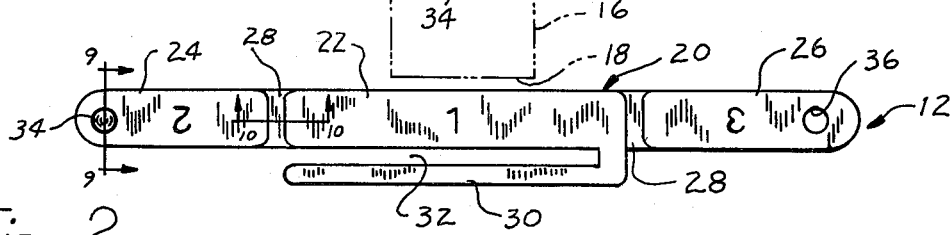
FIG. 2 is an elevational view of the clamp closure assembly according to this invention.

Referring now to the drawings, and particularly to FIGS. 1 and 2, FIG. 1 shows a flat fecal pouch or ostomy bag 10 having a clamp closure assembly 12 affixed to its lower drainage end. The bag 10 is made of a suitable elastomeric material and is adapted to be secured to a patient by means of a supporting device (not shown but disclosed in U.S. Pat. No. 2,818,069) secured within an inlet opening 14 formed in the upper portion of the pouch and a conventional belt support (not shown) secured to the supporting device. A lower end portion 16 (shown in phantom outline in FIG. 1 in its unwrapped condition) of the bag includes an inlet opening 18 through which waste is removed. Further details of the construction of the bag 10 may be found in U.S. Pat. No. 3,385,298, the subject matter of which is incorporated herein by reference.

The clamp closure assembly 12 comprises a flat, rectangular elongated strip 20 made of a suitable stiffly flexible plastic material. The strip 20 has a centrally located winding portion 22 provided with a pair of flat, rectangular closure wings 24 and 26 integral with and extending from the ends of the winding portion 22. Each wing 24 and 26 is hinged to the winding portion 22 by thinned zones 28 of separation so that the wings 24 and 26 may be folded to overlie the winding portion 22, as will become apparent.

The winding portion 22 includes slot means to receive the lower end opening portion 16 of the bag 10 so that the portion 16 of the bag 10 may be wound about the winding portion 22. In the illustrated embodiment, the slot means includes a finger 30 which is joined at one end to the winding portion 20 and which is parallel to on outside edge of the portion 20 to provide a space 32 for insertion of the lower end portion 16. Of course, the finger 30 may be joined at both ends to the winding portion 22, but such an arrangement would be more difficult with regard to the initial mounting operation.

Figure 3:
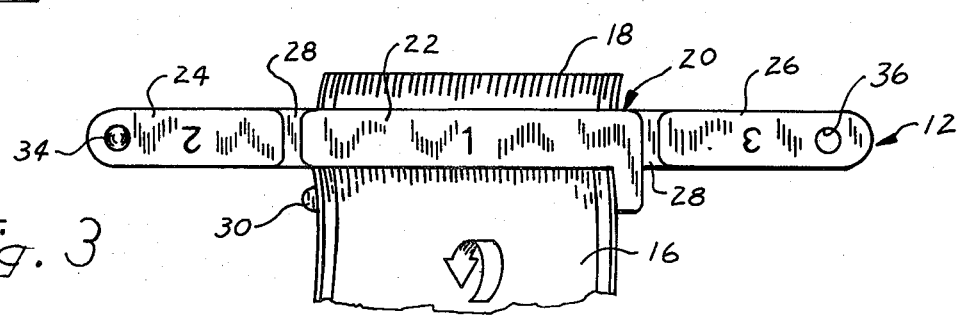
FIGS. 3 through 8 show the successive steps of winding and sealing the bottom drainage end of an ostomy bag.
Figure 4:
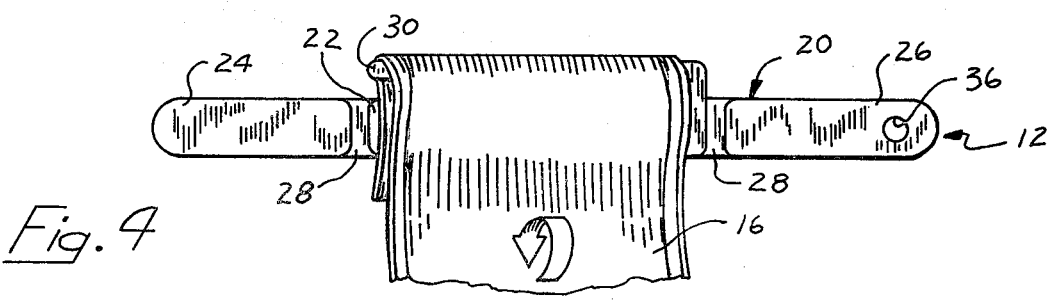
Figure 5:
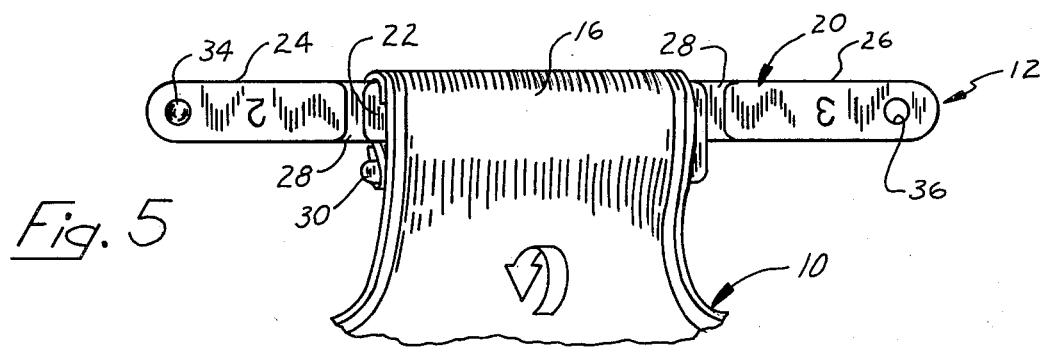
Figure 6:
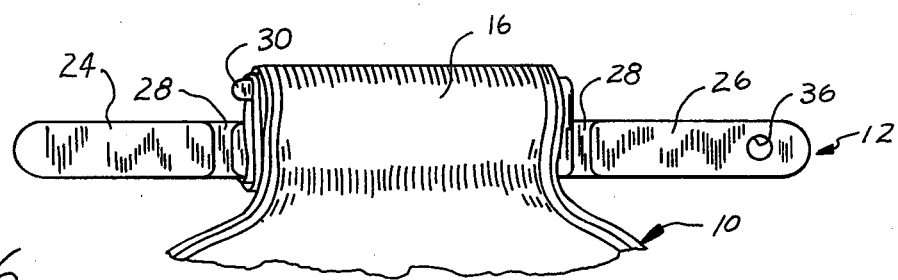
Figure 7:
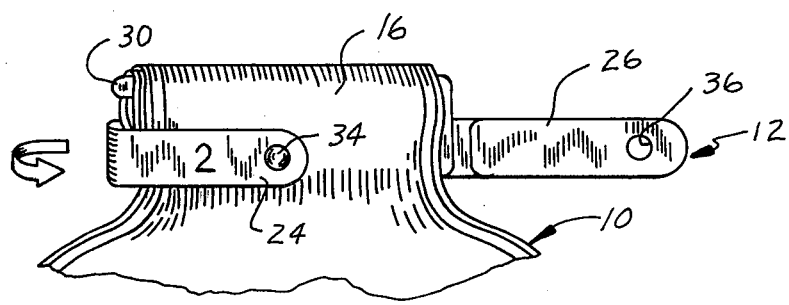
Figure 8:
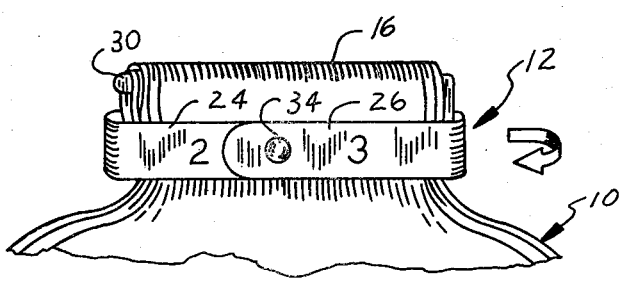
Figure 9:
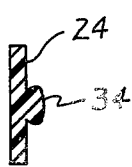
FIG. 9 is a cross-sectional view, the plane of the section being indicated by the line 9—9 in FIG. 2.
Figure 10:
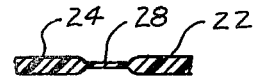
FIG. 10 is a cross-sectional view, the plane of the section being indicated by the line 10—10 in FIG. 2.

To facilitate the winding operation for a user, indicia such as the numerals "1", "2", and "3" may be placed on the winding portion 22, the wing 24, and the wing 26, respectively. As may be noted in FIGS. 2 through 8, the clamp assembly 12 is oriented in a position suitable for a winding operation as viewed by the user. Thus, the indicia "1" appears in its proper orientation relative to the user's view. The portion 16 of the bag 10 is then inserted through the space 32 and behind the winding portion 22 with approximately one-quarter inch of the portion 16 extending beyond the winding portion 22. As is indicated by the directional arrows in FIGS. 3, 4, and 5, the winding portion 1 is then turned so that the portion 16 of the bag 10 assumes the condition shown in FIG. 6. Typically, three 180-degree turns of the winding portion 22 are sufficient. The wing 24 is then folded over the winding portion 22 to securely clamp the now-wound lower end portion 16 of the bag against the winding portion 22. This operation exposes the indicia "2" to indicate to the user the second operation. The wing 26 is then folded over to expose the indicia "3", indicating to the user that the third and final operation has been performed, as is illustrated in FIG. 8. The wings 24 and 26 are then fastened together by pressing a bulbous-shaped peg 34 on the wing 24 through an aperture 36 in the wing 26.

The resulting clamped seal results in a secure closure arrangement for the drain opening of the bag, and provides an arrangement that can be easily manipulated by the user.

Although the preferred embodiment of this invention has been shown and described, it should be understood that various modifications and rearrangements of the parts may be resorted to without departing from the scope of the invention as disclosed and claimed herein.

What is claimed is:

1. A clamp closure assembly means for the lower end opening portion of an ostomy bag, comprising a flat, rectangular, elongated strip of stiffly flexible plastic material, said strip having a centrally located winding portion including at least one outside edge and a pair of flat, rectangular closure wings integral with and extending from the ends of said winding portion, each wing being hinged to said winding portion by thinned zones of separation so that said wings may be folded to overlie said winding portion, slot means adjacent said winding portion to receive a lower end opening portion of an ostomy bag so that said portion may be wound about said winding portion, means on each wing for attaching said wings together in a substantially superposed stacked position to overlie the winding portion and clamp the lower end portion of the bag after it has been wound against the winding portion of said strip, finger means separated from the winding portion by said slot means extending parallel to said outside edge for insertion of an ostomy bag, said closure assembly means being movable between an open condition for bag engagement and disengagement and a clamping position with said wings being attached together in said stacked position.

2. A clamp closure assembly according to claim 1, wherein said finger is fixed only at said one end to said winding portion.

3. A clamp closure assembly according to claim 1, wherein said means to attach said wings together comprises an aperture in one of said wings and a cooperating bulbous-shaped peg in the other of said wings.

4. A clamp closure assembly according to claim 1, including indicia on the faces of the winding portion and wings indicating the order of assembly steps to secure the clamp to the bag.

5. An assembly including an ostomy bag and a closure clamp for said bag, said ostomy bag comprising a pouch having a narrowed, elongated, lower end portion having a drain opening therein, said closure clamp comprising an elongated strip of stiffly flexible plastic material, said strip having a centrally located winding portion including at least one outside edge and a pair of closure wings integral with and extending from the ends of said winding portion, each wing being hinged to said winding portion by thinned zones of separation, slot means adjacent said winding portion to receive said lower end portion of said bag for winding and clamping, finger means separated from the winding portion by said slot means extending parallel to said outside edge for insertion of said lower end portion of the bag, said lower end portion of said bag being wound about said winding portion with said wings folded to overlie the winding portion and clamp the wound portion of the bag against said winding portion, means on each wing for attaching the wings together in a substantially superposed stacked position to securely clamp the wound portion of the bag against the winding portion of the strip, said closure clamp being movable from an open condition for bag engagement and disengagement to a clamping position with said wings being attached together in said stacked position.

* * * * *